US006278133B1

(12) United States Patent
Harris et al.

(10) Patent No.: US 6,278,133 B1
(45) Date of Patent: Aug. 21, 2001

(54) FIELD EFFECT TRANSISTOR OF SIC FOR HIGH TEMPERATURE APPLICATION, USE OF SUCH A TRANSISTOR AND A METHOD FOR PRODUCTION THEREOF

(75) Inventors: Christopher Harris, Sollentuna; Andrei Konstantinov; Susan Savage, both of Järfälla, all of (SE)

(73) Assignee: Acreo AB, Kista (SE)

( * ) Notice: Subject to any disclaimer, the term of this patent is extended or adjusted under 35 U.S.C. 154(b) by 0 days.

(21) Appl. No.: 09/298,116

(22) Filed: Apr. 23, 1999

(51) Int. Cl.[7] ............................................... H01L 31/0312
(52) U.S. Cl. ............................................ 257/77; 257/253
(58) Field of Search ........................................ 257/77, 253

(56) References Cited

U.S. PATENT DOCUMENTS

| | | |
|---|---|---|
| 4,769,338 | 9/1988 | Ovshinsky et al. . |
| 5,086,321 | 2/1992 | Batey . |
| 5,101,245 | 3/1992 | Shimura . |
| 5,448,085 * | 9/1995 | Calcatera et al. ................ 257/192 |
| 5,698,771 * | 12/1997 | Shields et al. ................... 73/31.05 |
| 5,705,826 | 1/1998 | Aratani et al. . |

\* cited by examiner

Primary Examiner—Sara Crane
(74) Attorney, Agent, or Firm—Dilworth & Barrese

(57) ABSTRACT

A field effect transistor of SiC for high temperature application has the source region layer (4), the drain region layer (5) and the channel region layer (6, 7) vertically separated from a front surface (14), where a gate electrode (12) is arranged, for reducing the electric field at said surface in operation of the transistor and in the case of operation as a gas sensor permitting all electrodes except for the gate electrode to be protected from the atmosphere.

23 Claims, 2 Drawing Sheets

FIELD EFFECT TRANSISTOR OF SIC FOR HIGH TEMPERATURE APPLICATION, USE OF SUCH A TRANSISTOR AND A METHOD FOR PRODUCTION THEREOF

The present invention relates to a field effect transistor of SiC for high temperature application having a source region layer, a drain region layer, a low doped channel region layer for conducting a current between the source region layer and the drain region layer, a gate electrode arranged to control the conduction properties of the channel region layer through varying the potential applied thereto as well as a front surface where the gate electrode is arranged, a use of such a transistor and a method for production thereof.

SiC has a number of properties that make it eminently suitable as a material in semiconductor devices, which have to function under extreme conditions. Its wide bandgap and high thermal stability, make it theoretically possible for semiconductor devices of SiC to function well at temperatures up to 1000 K. However, certain mechanisms in device structure can restrict the highest possible temperature of operation without failure to a much lower level.

Field effect transistors of SiC defined in the introduction and already known may fail at higher temperatures due to a charge injection mechanism. In the case of the presence of an insulating layer between the gate electrode and epitaxial layers of SiC, the energy barrier for electrons between the SiC conduction band edge and the insulating material (normally silicon dioxide) conduction band edge is small compared with for example silicon. This, coupled with the high electric fields encountered in SiC increases the chances of insulating layer breakdown caused by charge injection from the SiC into the insulating layer. This effect increases with temperature due to barrier lowering and can cause failure to occur at much lower temperatures than expected.

Another mechanism which has been previously noted to cause failure at higher temperatures is the reaction and consequent degradation of the contact metalization with gases in the surrounding atmosphere.

A possible use of a field effect transistor of SiC is as a gas sensor, for example in the flow of exhaust gases from cylinders of internal combustion engines of motor vehicles for sensing the composition of the exhaust gases passing. Such sensors already known may only withstand comparatively low temperatures without failure and have to be placed far from the cylinders at a point in the system where the exhaust gases have cooled significantly leading to long response times, and adjustment of individual cylinders is not possible as the sensors can only detect the joint output from the cylinders, SiC has as material a potential of enabling field effect transistors thereof to be placed near enough to monitor each cylinder separately with respect to the inherent thermal stability thereof. This would provide a much faster response time and the opportunity to adjust each cylinder individually in the event of it misfiring. This would lead to a reduction in petrol consumption and the production of cleaner exhaust gases, thus leading to a more environmentally-friendly system. It is pointed out that the invention is not at all restricted to this particular field of use, although it would be a very favourable application for a field effect transistor capable of withstanding very high temperatures.

SUMMARY OF THE INVENTION

The object of the present invention is to provide a field effect transistor of SiC having a stable operation at considerably higher temperatures than such transistors already known and which may be constructed to function as an advantageous gas sensor but also finds other possible applications.

This object is according to the invention obtained by arranging the source region layer, the drain region layer and the channel region layer vertically separated from said front surface for reducing the electric field at said surface in operation of the transistor.

Separation of the active source, drain and channel regions from the front surface reduces the electric field in the vicinity of said front surface. This means that the charge injection discussed above into said insulating layer when present on front surface is reduced and the insulating layer may withstand considerably higher temperatures than before, actually up to 800° C.

Furthermore, the sensitivity of the transistor operation to surface effects will be reduced, since the active regions thereof are separated from the surface.

Separation of the active regions from the front surface also permits placement of the gate electrode over the entire active area, the source and drain being contacted at a distance, so that when used as a gas sensor, all electrodes excepting the catalytic gate electrode may be protected from the atmosphere by the encapsulation and thus prolong their lifetime.

Another advantage is obtained by this removal of active regions from the surface, namely a discontinuous gate electrode may be used and the device will still function. This is a very important feature, since the gate metal layer may with time become discontinuous, but here it will still function and not fail as for other types of device. This also constitutes a preferred embodiment of the present invention.

According to another preferred embodiment of the invention the transistor comprises a first layer of SiC separating the source region layer and the drain region layer from said front surface and being low doped according to the same, first conductivity type as the source region layer and the drain region layer. Such a low doped layer may be used to efficiently control the conduction properties of the channel region layer through the gate potential and it provides the necessary features for a normally off and a normally on device, i.e. a device operating in enhancement mode and depletion mode, respectively. The doping concentration of said first layer is lower than $10^{16}$ cm$^{-3}$, preferably lower than $2 \times 10^{15}$ cm$^{-3}$.

According to another preferred embodiment of the invention both the source region layer and the drain region layer are buried in epitaxial layers of SiC and laterally separated for forming a lateral, i.e. horizontal, field effect transistor. Such a lateral transistor will have an advantageous function, and it will be possible to bury bars of source region layers and drain region layers alternating in the lateral direction in an interdigitated structure of such a transistor.

According to another preferred embodiment of the invention a second layer of SiC low-doped according to a second conductivity type opposite to the first one is arranged under the source region layer and the drain region layer for influencing the channel region layer arranged thereupon. The second layer and the gate electrode will in this way influence the channel region layer from opposite directions and thereby the appearance of a possible conducting channel between the source region layer and the drain region layer, so that a very sensitive transistor may be obtained.

According to another preferred embodiment of the invention one of the source region layer and the drain region layer is buried in epitaxial layers of SiC and the other one is arranged on a back side of the transistor opposite to said front surface for vertically separating the source region layer and the drain region layer for forming a vertical field effect transistor. Such a vertical transistor may in some applications be particularly advantageous.

According to another preferred embodiment of the invention said first conductivity type is n. This is preferred in cases in which the highest possible conductivity of the device is aimed at, since the mobility of electrons is much higher than that of holes in SiC. However, according to another preferred embodiment of the invention said first conductivity type is p. In some cases the conduction of holes may be preferred, and such a transistor may be more stable at high temperatures because of larger barrier heights, and when the transistor for example is used as a gas sensor it does riot matter that the total current will be lower, since the transistor only has to show variations in the current.

According to a very preferred embodiment of the invention the gate electrode is made of a catalytic metal, arranged at said front surface and exposed for being able to absorb specific gas atoms/molecules for influencing the potential of the gate electrode and allowing the transistor to function as a gas sensor. This is a very advantageous use of a transistor of this type for the reasons mentioned above, and the gate electrode may be exposed and the peak electric fields may still be removed from the front surface on which the gate electrode is arranged for stable operation of the transistor at very high temperatures.

According to a preferred embodiment of the invention constituting a further development of the embodiment last mentioned the catalytic gate metal is adapted to cause decomposition of hydrocarbons and absorb hydrogen. Such a transistor will be well suited to be used for sensing the presence of hydrocarbons in exhaust gases from cylinders in automobile engines at places where very high temperatures prevail for monitoring the function of each individual cylinder.

The invention also comprises a use of a transistor as above in environments in which temperatures above 500° C., preferably above 600° C. prevail, for example for sensing the composition of exhaust gases leaving cylinders in motor vehicles.

The invention also comprises a method for producing a field effect transistor of SiC for high temperature application, in which a source region layer and/or a drain region layer buried in layers of SiC epitaxially grown are produced in a first step by either implantation of dopants into a layer epitaxially grown or epitaxially growth while supplying dopants followed by a second step of epitaxial regrowth of a low doped layer of SiC on top thereof. A transistor of this type will be comparatively easy to manufacture.

Further advantages and advantageous features of the invention will appear from the following description and the other dependent claims.

BRIEF DESCRIPTION OF THE DRAWINGS

With reference to the appended drawings, below follows a description of preferred embodiments of the invention cited as examples.

In the drawings.

DETAILED DESCRIPTION OF PREFERRED EMBODIMENTS OF THE INVENTION

Figure 1:
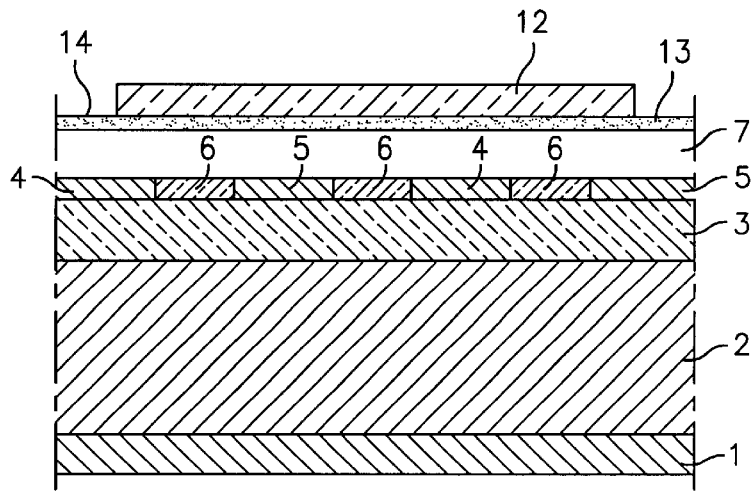
FIG. 1 is a schematic cross-section view of a lateral field effect transistor of SiC according to a first preferred embodiment of the invention.

A field effect transistor for high temperature application, especially but not exclusively suited for use as a gas sensor is shown in FIG. 1. This transistor has on top of a back side metallization layer 1 a substrate layer of SiC being doped p-type and a very low doped second layer 3, also of p-type on top thereof.

A source region layer 4 and a drain region layer 5 of n-type are arranged on top of the second layer 3 and laterally separated by a channel region layer 6 also doped n-type. A thin first layer 7 being very low-doped n-type is arranged on top of the layers 4–6. Contacts are made to the ends of the source and drain bars 4, 5 outside the area of the figure. A gate electrode 12 is arranged on top of the layers 4–7, and an insulating layer 13 of for instance $SiO_2$, $Si_3N_4$ or AlN may separate it from the first layer 7. In the case of use as a gas sensor, the gate electrode 12 is made of a catalytic metal such as platinum, palladium or iridium. The doping concentration of the first layer 7 and the second layer 3 is typically below $10^{16}$ cm$^{-3}$ and preferably below $2 \times 10^{15}$ cm$^{-3}$. The gate electrode 12 is adapted to control the conduction properties of the channel region layer 6 through the potential applied thereto and influences the channel region layer through the first layer 7, which for that reason has to be thin. The thicknesses of the first layer 7 and the second layer 3 may be 0,5 $\mu$m, whereas the thickness of the substrate layer 2 may be 300 $\mu$m, and the proportions of the different layers as shown in the figures have accordingly riot necessarily anything to do with the reality, but are mainly chosen for the sake of clear illustration. Thus, the channel region layer 6 will be influenced by the second layer 3 from below and by the gate electrode 12 from above. The device will run in either enhancement mode or depletion mode depending upon the doping level and thickness of channel region 6, i.e. it will be either a normally-off or a normally-on device.

Thanks to the buried channel 6 and the buried source region layer 4 and drain region layer 5 at a distance from the front surface 14 of the transistor the electric field at the surface will be reduced, so that charge injections into the insulating layer 13 is kept at a low level.

Thanks to the buried channel 6 and the buried source region layer 4 and drain region layer 5 at a distance from the front surface 14 of the transistor, the gate electrode may be applied over the entire active area and the source and drain electrodes applied at a distance, so that in the case of use as a gas sensor, only the gate electrode may be exposed to the atmosphere, the source and drain electrodes being protected by the packaging.

The function of this device as a hydrocarbon gas sensor is as follows. Should this device be of the normally-on type and run in depletion mode, a current will normally flow from the source region layer 4 to the drain region layer 5, through the channel region layer 6. If hydrocarbons appear in the atmosphere the catalytic metal of the gate electrode 12 will at the surface of the gate electrode decompose the gas molecules into gas ions, and the hydrogen ions will be absorbed by the gate metal and diffuse to the interface with the insulating layer 13 and thereby influence the work function of the gate electrode and accordingly the width of the conducting channel in the channel region layer 6 and thereby the current. This means that the presence of hydrocarbons in the exhaust gas flow may be measured by measuring such changes of the current.

Figure 4:
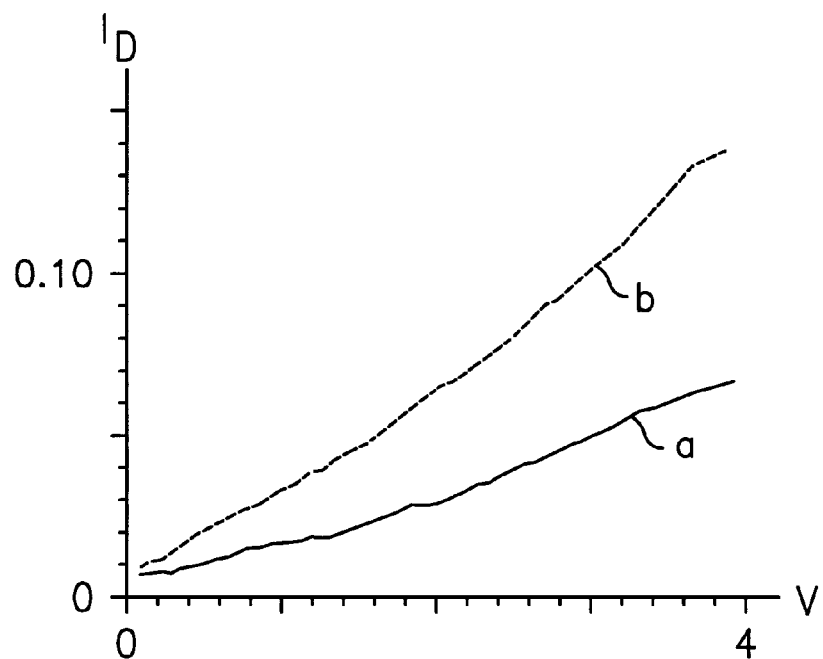
FIG. 4 is a graph illustrating the drain current as a function of the drain bias in a field effect transistor of SiC used as a gas sensor for the exposure of the gate electrode to two different gas compositions.
Figure 5:
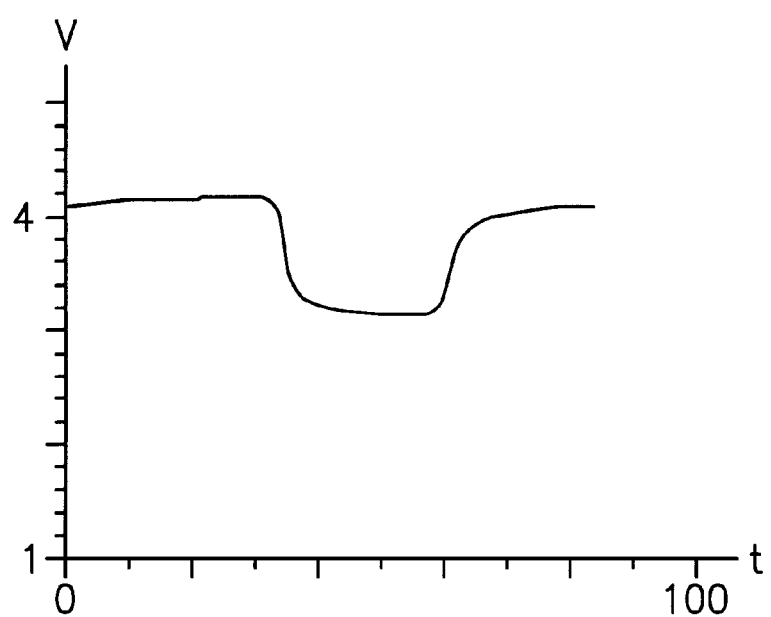
FIG. 5 is a graph illustrating a gas sensor response voltage versus time when a transistor concerned in FIG. 4 is exerted to a hydrogen pulse.

It is shown in FIGS. 4 and 5 how the presence of hydrocarbons may actually be detected and measured, and these graphs emanate from measurements carried out on field effect transistors of SiC produced by the present inventors and being of the type not that efficient in reducing the electric fields at the front surface 14 as the transistors according to the present invention The measurements were carried out at 600° C. FIG. 4 illustrates the drain current ID in mA versus the drain bias V in volts. The line a corresponds to 1% $O_2$ and the line b 3% $H_2$+1% $O_2$ in the atmosphere to which the gate metal was exposed. in practice, the gas response, i.e. the response to a hydrogen pulse, was measured by maintaining the current level at 100 $\mu$A and measuring the change in the voltage drop between the source and the drain contacts with the substrate grounded. A voltage change of approximately 1V was measured. FIG. 5 is a graph of the voltage across the source and drain V in volts versus the time in seconds during the measurement just described at a constant drain current of 0,1 mA, in which a hydrogen pulse is given after about 30 seconds.

Figure 2:
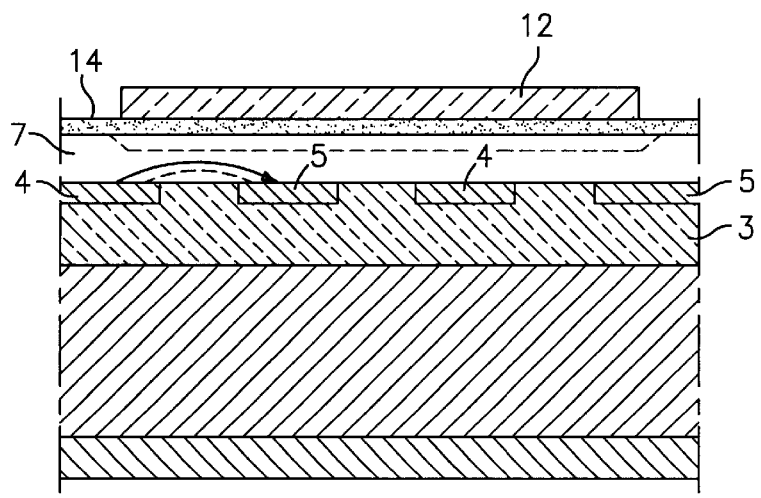
FIG. 2 is a schematic cross-section view of a lateral field effect transistor of SiC according to a second preferred embodiment of the invention.

FIG. 2 illustrates a transistor according to a second preferred embodiment of the invention differing from the one shown in FIG. 1 only by the fact that the low doped second layer 3 extends to the first layer 7 while separating the source region layer 4 and the drain region layer 5. This means that the conducting channel will in this transistor be formed in the first layer 7 between the dashed lines illustrating how the second layer 3 and the gate 12 depletes the first layer 7 from opposite directions.

Figure 3:
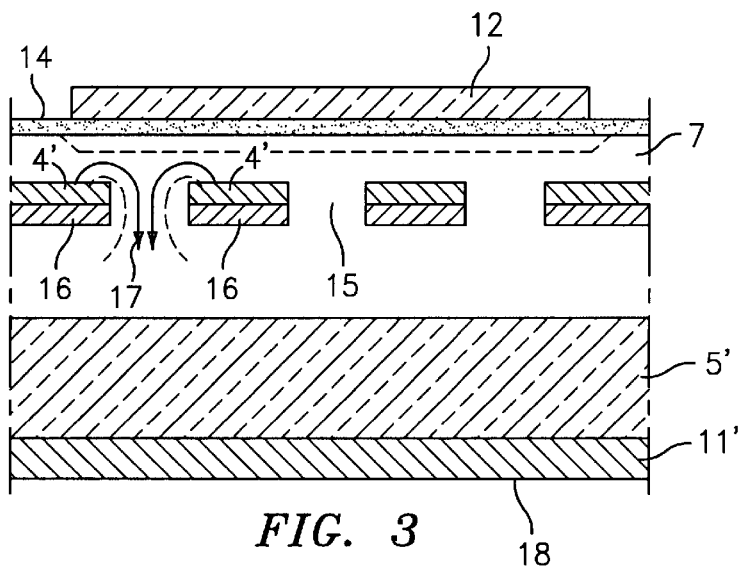
FIG. 3 is a schematic cross-section view of a vertical field effect transistor of SiC according to a third preferred embodiment of the invention.

A transistor according to a third preferred embodiment of the invention is illustrated in FIG. 3, and this is a vertical device, in which the very low doped n-type layer 7 extends to the substrate layer 5' being here of n-type and forming the drain region layer on a back: side 18 of the device. Source region layers 4' are buried in the first layer 7 and laterally separated by a portion 15 thereof. Furthermore, third layers 16 being highly p-type doped are arranged under the source region layer 4', and may even extend beyond the source region layer 4, and the third layers 16 will deplete parts of the first layer and form a vertical channel as illustrated through the dashed lines for a current flow according to the lines 17 from the source region layer to the drain region layer. Furthermore, this conducting channel will be influenced by the potential of the gate electrode, since the layer 7 is low doped and comparatively thin.

Another advantage of removing the source region layer and the drain region layer as well as the channel from the front surface 14 of the device is that it will be possible to enclose the entire structure except for the catalytic gate metal inside a packaging, thus protecting critical contact regions from the atmosphere. This should result in a significant performance improvement and further improve the temperature stability of such a transistor.

A transistor according to the present invention will have a stable operation at very high temperatures, up to at least 800° C., which makes it possible to use for example as a gas sensor in the exhaust gas flow of an automobile engine in the immediate vicinity of the cylinders for monitoring each cylinder separately by the application of a catalytic gate metal to the front surface. This provides a fast response time and the opportunity to adjust each cylinder individually in the event of misfiring. However, a transistor of this type may find other applications where very high temperatures prevail, and the gate electrode may then be made of either another catalytic metal or a non-reactive metal when the potential of the gate may be controlled by an external source.

The transistor may be produced in the following way: Starting with a high-doped substrate (either n- or p-type), a low-doped layer of suitable conductivity type is grown through for instance CVD on one side of the substrate. The highly-doped source and drain region layers are then formed, either by implantation and anneal of suitable doping elements, or by epitaxial growth and etching. Another low-doped epitaxial layer of suitable conductivity type is then grown on top thereof. This is followed by processing of a gate oxide or other insulating layer if required, ohmic contacts to the source, the drain and the backside of the device, and the gate metal. Suitable dopants are for example: donors: N and P, acceptors: Al and B. "High-doped" means typically a doping concentration above $10^{19}$ cm$^{-3}$, preferably above $10^{20}$ cm$^{-3}$.

The invention is of course not in any way restricted to the preferred embodiments described above, but many possibilities to modifications thereof would be apparent to a man with ordinary skill in the art without departing from the basic idea of the invention as defined in the appended claims.

The doping types may be changed, i.e. n-type for p-type and conversely, in all the embodiments shown as already described above, and this may be of particular interest when the transistor is used as a gas sensor.

"Channel region layer" as used here and in the claims is to be interpreted broadly and defines the later in which a conducting channel is created, and "the channel region layer is vertically separated from the front surface" also includes for instance the embodiment according to FIG. 2, in which the conducting channel is separated from the front surface although the first layer in which the conducting channel is formed extends to the front surface. Accordingly, the channel region layer is there to be understood as a lower sub-layer of first layer.

"Catalytic metal" is defined as a metal being at least able to absorb gas molecules/atoms and possibly also cause decomposition of gas molecules.

What is claimed is:

1. A field effect transistor of SiC for high temperature application having a source region layer (4,4'), a drain region layer (5,5') a low doped channel region layer (6, 7) for conducting a current between the source region layer and the drain region layer, a gate electrode (12) arranged to control the conduction properties of the channel region layer through varying the potential applied thereto as well as a front surface (14) where the gate electrode is arranged, characterized in that the source region layer, the drain region layer and the channel region layer are vertically separated from said front surface for reducing the electric field at said surface in operation of the transistor, said transistor comprises a first layer (7) of SiC separating the source region layer (4,4') and the drain region layer (5,5') from said front surface (14) and being low doped according to the same, first conductivity type as the source region layer and the drain region layer, and the doping concentration of said first layer (7) is lower than $10^{16}$ cm$^{-3}$.

2. A transistor according to claim 1, characterized in that the gate electrode (12) is arranged on said front surface (14).

3. A field effect transistor of SiC for high temperature application having a source region layer (4,4'), a drain region layer (5,5'), a low doped channel region layer (6,7) for conducting a current between the source region layer and the drain region layer, a gate electrode (12) arranged to control the conduction properties of the channel region layer through varying the potential applied thereto as well as a front surface (14) where the gate electrode is arranged, characterized in that the source region layer, the drain region layer and the channel region layer are vertically separated from said front surface for reducing the electric field at said surface in operation of the transistor, said transistor comprises a first layer (7) of SiC separating the source region layer (4,4') and the drain region layer (5,5') from said front surface (14) and being low doped according to the same, first conductivity type as the source region layer and the drain region layer, and the gate electrode(12) is separated from the low doped first layer (7) by an insulating layer (13).

4. A transistor according to claim 1, characterized in that both the source region layer (4) and the drain region layer (5) are buried in epitaxial layers of SiC and laterally separated for forming a lateral, field effect transistor.

5. A field effect transistor of SiC for high temperature application having a source region layer (4,4'), a drain region layer (5,5'), a low doped channel region layer (6,7) for conducting a current between the source region layer and the drain region layer, a gate electrode (12) arranged to control the conduction properties of the channel region layer through varying the potential applied thereto as well as a front surface (14) where the gate electrode is arranged , characterized in that the source region layer, the drain region layer, and the channel region layer are vertically separated from said front surface for reducing the electric field at said surface in operation of the transistor, both the source region layer (4) and the drain region layer (5) are buried in epitaxial layers of SiC and laterally separated for forming a lateral field effect transistor, and a second layer (3) of SiC low-doped according to a second conductivity type opposite to the first one is arranged under the source region layer (4) and the drain region layer (5) for influencing the channel region layer (6,7) arranged thereupon.

6. A transistor according to claim 5, characterized in that the gate electrode (12) and said second layer (13) are arranged to influence the channel region layer from above and below, respectively.

7. A transistor according to claim 5, characterized in that the source region layer (4) and the drain region layer (5) are separated by portions of said second layer (3).

8. A transistor according to claim 5, characterized in that the source region layer (4) and the drain region layer (5) are separated by a portion (6) of said first layer having a higher doping concentration than the rest of said first layer arranged thereabove.

9. A transistor according to claim 5, characterized in that said first layer (7) is adapted to comprise the channel region layer.

10. A field effect transistor of SiC for high temperature application having a source region layer (4,4'), a drain region layer (5,5'), a low doped channel region layer (6,7) for conducting a current between the source region layer and the drain region layer, a gate electrode (12) arranged to control the conduction properties of the channel region layer through varying the potential applied thereto as well as a front surface (14) where the gate electrode is arranged, characterized in that the source region layer, the drain region layer and the channel region layer are vertically separated from said front surface for reducing the electric field at said surface in operation of the transistor, and one of the source region layer (4') and the drain region layer is buried in epitaxial layers (7) of SiC and the other one (5') is arranged on a back side (18) of the transistor opposite to said front surface (14) for vertically separating the source region layer and the drain region layer for forming a vertical field effect transistor.

11. A transistor according to claim 10, characterized in that said buried one (4') of the source region layer and the drain region layer has portions laterally separated by a layer (7) of SiC being low-doped according to the first conductivity type for forming a vertical channel extending between said portions from the source region layer (4') to the drain region layer (5').

12. A transistor according to claim 11, characterized in that a third layer (16) doped according to a second conductivity type is arranged under the buried one (4') of the source region layer and the drain region layer under said portions for influencing the vertical channel formed therebetween.

13. A transistor according to claim 5, characterized in that said first conductivity type is n.

14. A transistor according to claim 5, characterized in that said first conductivity type is p.

15. A transistor according to claim 5, characterized in that it is adapted to be run either in enhancement or depletion mode.

16. A transistor according to claim 5, characterized in that the gate electrode (12) is made of a catalytic metal, arranged at said front surface and exposed for being able to absorb specific gas atoms/molecules for influencing the potential of the gate electrode and allowing the Transistor to function as a gas sensor.

17. A transistor according to claim 16, characterized in that the catalytic gate metal is adapted to cause decomposition of hydrocarbons and absorb hydrogen.

18. A transistor according to claim 5, structured and arranged for use in environments where temperatures above 500° C. prevail.

19. A transistor according to claim 18, characterized in that the transistor is structured and arranged for use in an atmosphere for sensing gas composition thereof.

20. A transistor according to claim 19, characterized in that the transistor is inserted in the flow of exhaust gases from cylinders of engines of motor vehicles for sensing the composition of the exhaust gases passing.

21. A transistor according to claim 18, structured and arranged for use in environments where temperatures above 600° C. prevail.

22. A transistor according to claim 1, characterized in that the doping concentration of said first layer (7) is lower than $2\times10^{15}$ cm$^{-3}$.

23. A transistor according to claim 4, characterized in that both the source region layer (4) and the drain region layer (5) are laterally separated for forming a horizontal field effect transistor.

* * * * *